US011129727B2

United States Patent
Richter et al.

(10) Patent No.: US 11,129,727 B2
(45) Date of Patent: Sep. 28, 2021

(54) INFLATABLE NON-DISTRACTING INTERVERTEBRAL IMPLANTS AND RELATED METHODS

(71) Applicant: Medos International Sarl, Le Locle (CH)

(72) Inventors: Joern Richter, Kandern (DE); J. Riley Hawkins, Cumberland, RI (US); Thomas Gamache, Westport, MA (US); Sean Hamilton Kerr, Oreland, PA (US); Mark Thomas Fulmer, Glenmoore, PA (US)

(73) Assignee: Medos International Sari, Le Locle (CH)

( * ) Notice: Subject to any disclaimer, the term of this patent is extended or adjusted under 35 U.S.C. 154(b) by 0 days.

(21) Appl. No.: 16/370,105

(22) Filed: Mar. 29, 2019

(65) Prior Publication Data

US 2020/0306052 A1 Oct. 1, 2020

(51) Int. Cl.
*A61F 2/44* (2006.01)
*A61B 17/70* (2006.01)
*A61F 2/30* (2006.01)

(52) U.S. Cl.
CPC .......... *A61F 2/441* (2013.01); *A61B 17/7097* (2013.01); *A61F 2/442* (2013.01);
(Continued)

(58) Field of Classification Search
CPC ........... A61F 2/441; A61F 2002/30583; A61B 17/7097
(Continued)

(56) References Cited

U.S. PATENT DOCUMENTS 4,573,448 A 3/1986 Kambin
4,646,738 A 3/1987 Trott
(Continued)

FOREIGN PATENT DOCUMENTS

CN 102727309 B 11/2014
DE 9415039 U1 11/1994
(Continued)

OTHER PUBLICATIONS

International Search Report and Written Opinion for Application No. PCT/US2015/043554, dated Nov. 19, 2015 (8 pages).
(Continued)

*Primary Examiner* — Eduardo C Robert
*Assistant Examiner* — David C Comstock
(74) *Attorney, Agent, or Firm* — Barnes & Thornburg LLP

(57) ABSTRACT

Inflatable orthopedic implants and related methods are disclosed herein, e.g., for deploying such implants within an intervertebral space for use in spinal fusion surgery, other intervertebral surgical procedures, or other surgical procedures. The inflatable intervertebral implant can include a hollow inflatable body that can be configured in a compact state for insertion into a target intervertebral space between a pair of adjacent vertebral bodies. Once the vertebral bodies are separated or distracted, e.g., using one or more inflatable distractors, the hollow body of the inflatable implant can be inflated with bone cement or other curable material. When the curable material hardens, the inflated implant can form a rigid intervertebral support structure (e.g., a fusion cage) capable of maintaining the vertebral distraction and thereby enabling removal of the distractors.

29 Claims, 11 Drawing Sheets

(52) U.S. Cl.
CPC ............ *A61F 2002/30537* (2013.01); *A61F 2002/30581* (2013.01)

(58) Field of Classification Search
USPC .................................................. 623/17.12
See application file for complete search history.

(56) References Cited

U.S. PATENT DOCUMENTS

| | | |
|---|---|---|
| 4,678,459 A | 7/1987 | Onik et al. |
| 4,863,430 A | 9/1989 | Klyce et al. |
| 4,888,146 A | 12/1989 | Dandeneau |
| 5,080,662 A | 1/1992 | Paul |
| 5,195,541 A | 3/1993 | Obenchain |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,662,300 A | 9/1997 | Michelson |
| 5,688,222 A | 11/1997 | Hluchy et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey, Jr. et al. |
| 5,954,635 A | 9/1999 | Foley et al. |
| 6,033,105 A | 3/2000 | Barker et al. |
| 6,053,907 A | 4/2000 | Zirps |
| 6,063,021 A | 5/2000 | Hossain et al. |
| 6,110,182 A | 8/2000 | Mowlai-Ashtiani |
| 6,200,322 B1 | 3/2001 | Branch et al. |
| 6,217,509 B1 | 4/2001 | Foley et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,558,407 B1 | 5/2003 | Ivanko et al. |
| 6,575,899 B1 | 6/2003 | Foley et al. |
| 6,579,281 B2 | 6/2003 | Palmer et al. |
| 6,582,467 B1 * | 6/2003 | Teitelbaum ........... A61F 2/4465 623/17.11 |
| 6,626,830 B1 | 9/2003 | Califiore et al. |
| 6,648,915 B2 | 11/2003 | Sazy |
| 6,676,597 B2 | 1/2004 | Guenst et al. |
| 6,688,564 B2 | 2/2004 | Salvermoser et al. |
| 6,758,809 B2 | 7/2004 | Briscoe et al. |
| 6,808,505 B2 | 10/2004 | Kadan |
| 6,887,198 B2 | 5/2005 | Phillips et al. |
| 6,983,930 B1 | 1/2006 | La Mendola et al. |
| 7,087,058 B2 | 8/2006 | Cragg |
| 7,104,986 B2 | 9/2006 | Hovda et al. |
| 7,137,949 B2 | 11/2006 | Scirica et al. |
| 7,182,731 B2 | 2/2007 | Nguyen et al. |
| 7,341,556 B2 | 3/2008 | Shalman |
| 7,341,601 B2 | 3/2008 | Eisermann et al. |
| 7,434,325 B2 | 10/2008 | Foley et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,771,384 B2 | 8/2010 | Ravo |
| 7,794,456 B2 | 9/2010 | Sharps et al. |
| 7,799,079 B2 | 9/2010 | Hestad et al. |
| 7,811,303 B2 | 10/2010 | Fallin et al. |
| 7,931,579 B2 | 4/2011 | Bertolero et al. |
| 7,946,981 B1 | 5/2011 | Cubb |
| 7,951,141 B2 | 5/2011 | Sharps et al. |
| 7,959,564 B2 | 6/2011 | Ritland |
| 7,988,623 B2 | 8/2011 | Pagliuca et al. |
| 7,993,404 B2 * | 8/2011 | Trieu ................ A61B 17/7059 623/17.12 |
| 8,007,492 B2 | 8/2011 | DiPoto et al. |
| 8,007,535 B2 * | 8/2011 | Hudgins ............ A61F 2/4601 623/17.12 |
| 8,021,426 B2 | 9/2011 | Segal et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,083,800 B2 | 12/2011 | Edie |
| 8,092,464 B2 | 1/2012 | McKay |
| 8,092,536 B2 | 1/2012 | Ahrens et al. |
| 8,096,944 B2 | 1/2012 | Harrel |
| 8,128,698 B2 | 3/2012 | Bentley et al. |
| 8,152,813 B2 | 4/2012 | Osorio et al. |
| 8,202,216 B2 | 6/2012 | Melkent et al. |
| 8,236,006 B2 | 8/2012 | Hamada |
| 8,262,738 B2 | 9/2012 | Melkent |
| 8,317,865 B2 | 11/2012 | Osorio et al. |
| 8,333,690 B2 | 12/2012 | Ikeda |
| 8,337,556 B2 | 12/2012 | Shaolian et al. |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,480,718 B2 | 7/2013 | Protopsaltis et al. |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,622,894 B2 | 1/2014 | Banik et al. |
| 8,632,593 B2 * | 1/2014 | Suh ..................... A61F 2/30721 623/17.12 |
| 8,636,655 B1 | 1/2014 | Childs |
| 8,690,764 B2 | 4/2014 | Clark et al. |
| 8,709,074 B2 | 4/2014 | Solem et al. |
| 8,721,536 B2 | 5/2014 | Marino et al. |
| 8,740,779 B2 | 6/2014 | Yoshida |
| 8,747,475 B2 | 6/2014 | Kuslich |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,300 B2 | 1/2015 | Shadduck et al. |
| 8,932,360 B2 | 1/2015 | Womble et al. |
| 8,936,605 B2 | 1/2015 | Greenberg |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,126,023 B1 | 9/2015 | Sahatjian et al. |
| 9,131,948 B2 | 9/2015 | Fang et al. |
| 9,144,374 B2 | 9/2015 | Maurice, Jr. |
| 9,198,674 B2 | 12/2015 | Benson et al. |
| 9,211,059 B2 | 12/2015 | Drach et al. |

(56) References Cited

U.S. PATENT DOCUMENTS

| | | |
|---|---|---|
| 9,216,016 B2 | 12/2015 | Fiechter et al. |
| 9,216,125 B2 | 12/2015 | Sklar |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| 9,333,087 B2 | 5/2016 | Lambrecht |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,492,278 B2 | 11/2016 | Wei et al. |
| 9,510,853 B2 | 12/2016 | Aljuri et al. |
| 9,526,401 B2 | 12/2016 | Saadat et al. |
| 9,545,321 B2 | 1/2017 | Hibri et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 9,833,273 B2 | 12/2017 | Sennett et al. |
| 2002/0022762 A1 | 2/2002 | Beane et al. |
| 2002/0077701 A1* | 6/2002 | Kuslich .................. A61F 2/442 623/17.12 |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2004/0225296 A1 | 11/2004 | Reiss et al. |
| 2004/0230309 A1* | 11/2004 | DiMauro ................ A61F 2/442 623/17.12 |
| 2005/0085692 A1 | 4/2005 | Kiehn et al. |
| 2005/0090848 A1 | 4/2005 | Adams |
| 2005/0187570 A1 | 8/2005 | Nguyen et al. |
| 2005/0256525 A1 | 11/2005 | Culbert et al. |
| 2006/0106459 A1 | 5/2006 | Truckai et al. |
| 2006/0206118 A1 | 9/2006 | Kim et al. |
| 2006/0253200 A1 | 11/2006 | Bao et al. |
| 2007/0055259 A1 | 3/2007 | Norton et al. |
| 2007/0055278 A1 | 3/2007 | Osorio et al. |
| 2007/0129634 A1 | 6/2007 | Hickey et al. |
| 2007/0149975 A1 | 6/2007 | Oliver et al. |
| 2007/0150059 A1* | 6/2007 | Ruberte .................. A61F 2/441 623/17.12 |
| 2007/0173940 A1* | 7/2007 | Hestad .................. A61F 2/4465 623/17.12 |
| 2007/0203396 A1 | 8/2007 | McCutcheon et al. |
| 2007/0225556 A1 | 9/2007 | Ortiz et al. |
| 2007/0225705 A1 | 9/2007 | Osorio et al. |
| 2007/0233258 A1 | 10/2007 | Hestad et al. |
| 2007/0260113 A1 | 11/2007 | Otawara |
| 2008/0015621 A1 | 1/2008 | Emanuel |
| 2008/0033251 A1 | 2/2008 | Araghi |
| 2008/0065190 A1 | 3/2008 | Osorio et al. |
| 2008/0081951 A1 | 4/2008 | Frasier et al. |
| 2008/0183292 A1 | 7/2008 | Trieu |
| 2008/0188714 A1 | 8/2008 | McCaffrey |
| 2008/0249604 A1* | 10/2008 | Donovan ............ A61B 17/8811 606/249 |
| 2009/0018566 A1 | 1/2009 | Escudero et al. |
| 2009/0024158 A1 | 1/2009 | Viker |
| 2009/0048678 A1 | 2/2009 | Saal et al. |
| 2009/0062871 A1 | 3/2009 | Chin et al. |
| 2009/0076517 A1 | 3/2009 | Reiley et al. |
| 2009/0105543 A1 | 4/2009 | Miller et al. |
| 2009/0112221 A1 | 4/2009 | Burke et al. |
| 2009/0112323 A1* | 4/2009 | Hestad .................. A61F 2/4611 623/17.12 |
| 2009/0156898 A1 | 6/2009 | Ichimura |
| 2009/0182427 A1 | 7/2009 | Liu et al. |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0042151 A1 | 2/2010 | Anderson |
| 2010/0076476 A1 | 3/2010 | To et al. |
| 2010/0082036 A1 | 4/2010 | Reiley et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0168755 A1 | 7/2010 | Reiley et al. |
| 2010/0174328 A1 | 7/2010 | Seaton, Jr. et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2011/0004307 A1* | 1/2011 | Ahn ........................ A61F 2/441 623/17.12 |
| 2011/0028791 A1 | 2/2011 | Marino et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0184422 A1* | 7/2011 | Mathews ............... A61M 25/10 606/90 |
| 2011/0251615 A1 | 10/2011 | Truckai et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0066940 A1 | 3/2014 | Fang et al. |
| 2014/0067066 A1 | 3/2014 | Kuslich |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275799 A1 | 9/2014 | Schuele |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2014/0378980 A1 | 12/2014 | Lomeli et al. |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |

(56) References Cited

U.S. PATENT DOCUMENTS

| | | |
|---|---|---|
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0056195 A1 | 3/2017 | Lutz et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2017/0360570 A1 | 12/2017 | Berndt et al. |

FOREIGN PATENT DOCUMENTS

| | | |
|---|---|---|
| DE | 29916026 U1 | 11/1999 |
| EP | 0537116 A1 | 4/1993 |
| EP | 0807415 A2 | 11/1997 |
| EP | 764008 B1 | 2/2004 |
| GB | 2481727 A | 1/2012 |
| WO | 96/29014 A1 | 9/1996 |
| WO | 2001/056490 A1 | 8/2001 |
| WO | 2001/089371 A1 | 11/2001 |
| WO | 2002/002016 A1 | 1/2002 |
| WO | 2004/103430 A2 | 12/2004 |
| WO | 2007078692 A2 | 7/2007 |
| WO | 2008/121162 A1 | 10/2008 |
| WO | 2009/033207 A1 | 3/2009 |
| WO | 2010063111 A1 | 6/2010 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2016/111373 A1 | 7/2016 |
| WO | 2016/131077 A1 | 8/2016 |
| WO | 2016/168673 A1 | 10/2016 |
| WO | 2017/006684 A1 | 1/2017 |
| WO | 2017/015480 A1 | 1/2017 |
| WO | 2017/083648 A1 | 5/2017 |

OTHER PUBLICATIONS

International Search Report and Written Opinion for Application No. PCT/US2015/048485, dated Feb. 9, 2016. (16 pages).
International Search Report and Written Opinion for Application No. PCT/US2015/060978, dated Feb. 15, 2016 (8 pages).
Invitation to Pay Additional Fees for Application No. PCT/US2016/050022, dated Nov. 3, 2016 (2 pages).
International Search Report and Written Opinion for Application No. PCT/US2016/050022, dated Feb. 1, 2017 (19 pages).
International Search Report and Written Opinion for Application No. PCT/EP2020/057873, dated Jun. 30, 2020 (10 pages).
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Jung, K., et al., "A hands-free region-of-interest selection interface for solo surgery with a wide-angle endoscope: preclinical proof of concept," Surg Endosc, 2017, v. 31, pp. 974-980.

* cited by examiner

INFLATABLE NON-DISTRACTING INTERVERTEBRAL IMPLANTS AND RELATED METHODS

FIELD

The present disclosure relates generally to orthopedic implants and, more particularly, to inflatable orthopedic implants and related methods of deploying inflatable implants, e.g., for spinal fusion or other intervertebral surgical procedures.

BACKGROUND

Degenerative changes in the spine can cause the loss of normal structure and/or function. The intervertebral disc is one structure prone to the degenerative changes associated with wear and tear, aging, and even misuse. Over time the collagen (protein) structure of the intervertebral disc weakens and may become structurally unsound. Additionally, the water and proteoglycan (the molecules that attract water) content decreases, thereby narrowing the space between the adjacent vertebrae, which can result in nerve root compression and pain. These changes can lead to the disc's inability to handle mechanical stress.

One form of treatment available for degenerative disc disease is spinal fusion surgery, which involves the surgical removal of a portion or all of an intervertebral disc followed by fusion of the adjacent vertebrae. An intervertebral orthopedic implant, e.g. a fusion cage, is often placed between the two adjacent vertebrae to fill the intervertebral space left by the removed disc and to allow bone to grow between the adjacent vertebrae.

Spinal fusion procedures can present the surgeon with several challenges, especially where the disc is severely degenerative. When the natural disc is removed, the adjacent vertebral bodies collapse upon each other, thereby requiring separation of the vertebral bodies to enable placement of a fusion cage. However, separation or distraction of the vertebral bodies beyond a certain degree can result in further injury or damage to the vertebrae. Conversely, where the disc is severely degenerative, the narrow disc space and lack of elasticity between the vertebrae can hinder the surgeon's ability to separate the vertebrae to a height sufficient to enable placement of the fusion cage.

To overcome some of these problems, specialized mechanical tools have been developed to facilitate the placement of a fusion cage between adjacent vertebral bodies of a patient's spine. Among the known tools for performing such procedures are spinal distracters, e.g. spreaders and insertion devices. In general, the spreader is placed between adjacent vertebrae, and then used to pry the vertebrae apart. Once the space between the vertebral bodies is sufficient to enable placement of a fusion cage, the cage can then be inserted, either manually or with an insertion tool, into the space to hold the adjacent vertebrae apart. Typically, cancellous bone is packed in and/or around the cage to promote fusion of the adjacent vertebrae.

While most spreader devices are effective to assist surgeons with the placement of fusion cages, the use of such tools can prove cumbersome and not necessarily conducive for minimally invasive surgical (MIS) procedures. For example, insertion of a spreader device into the limited disc space can cause fracture of a vertebra. Moreover, once inserted, the spreaders can cause over-distraction of the vertebral bodies, or can hinder placement of the fusion cage. In the presence of degenerative disease or chronic changes where the disc space has become narrow, it can be difficult to maintain an adequate interbody height and, at the same time, insert and position the cage.

There remains a continued need for improved orthopedic implants and related methods to facilitate the safe and accurate insertion of an implant between adjacent vertebral bodies while minimizing invasiveness and the risk of further injury to the patient.

SUMMARY

Inflatable orthopedic implants and related methods are disclosed herein, e.g., for deploying such implants within an intervertebral space for use in spinal fusion surgery, other intervertebral surgical procedures, or other surgical procedures.

The inflatable intervertebral implant can include a hollow inflatable body that can be configured in a compact state for insertion into a target intervertebral space between a pair of adjacent vertebral bodies. Once the vertebral bodies are separated or distracted, e.g., using one or more inflatable distractors, the hollow body of the inflatable implant can be inflated with bone cement or other curable material. When the curable material hardens, the inflated implant can form a rigid intervertebral support structure (e.g., a fusion cage) capable of maintaining the vertebral distraction and thereby enabling removal of the distractors.

In some embodiments, an inflatable implant can be deployed for corrective angulation between adjacent vertebral bodies. Such angular correction can be useful to reverse various deformities of the spine, including but not limited to scoliosis or other conditions that produce abnormal lordotic, kyphotic, or other spinal angles. In some embodiments, an inflatable orthopedic implant can be deployed in an intervertebral space in a minimally invasive manner. Although the inflatable orthopedic implants are disclosed for use in spinal fusion surgery, one skilled in the art will recognize that the inflatable implants can be readily modified and deployed for use in other intervertebral surgical procedures, or other surgical procedures in other portions of the body.

In one aspect, a method of deploying an inflatable implant is provided that can include inserting an inflatable implant into an intervertebral space between anterior portions of adjacent vertebral bodies, inserting an inflatable distractor into the intervertebral space between posterior portions of the adjacent vertebral bodies, and inflating the distractor such that the inflated distractor can exert a force against the posterior portions of the adjacent vertebral bodies and thereby separate the adjacent vertebral bodies. The method can further include inflating the implant after the distractor separates the adjacent vertebral bodies to form an intervertebral support structure having an arcuate shape that can fill the intervertebral space between the anterior portions of the adjacent vertebral bodies.

The inflatable implant and methods described herein can include any of a variety of additional or alternative features, all of which are considered within the scope of the present disclosure. For example, in some embodiments, the implant can be inflated with a curable material. By way of further example, in certain embodiments, the method can further include deflating the inflated distractor within the intervertebral space after the inflated implant hardens and withdrawing the deflated distractor from the intervertebral space. The inflated implant can remain within the intervertebral space to provide support between the anterior portions of the adjacent vertebral bodies after withdrawal of the distractor. The distractor can be inflated to a size that can separate the adjacent vertebral bodies by a desired height.

In some embodiments, the method can further include inflating multiple distractors. Moreover, in certain embodiments, each of the distractors can be inflated to a respective size to adjust an angle between the adjacent vertebral bodies in a sagittal plane. In certain embodiments, each of the distractors can be inflated to a respective size to adjust an angle between the adjacent vertebral bodies in a frontal plane.

In some embodiments, the method can further include filling the intervertebral space with a fusion material that can facilitate bone growth between the adjacent vertebral bodies. In some embodiments, the inflatable implant can be rolled, folded, or collapsed when inserted into the intervertebral space.

In some embodiments, the intervertebral support structure can include an anterior side wall having a first shape, a posterior side wall having a second shape, a superior bearing surface and an inferior bearing surface, and a lateral end wall and a medial end wall. Each bearing surface can extend transversely between the anterior wall and the posterior wall. In certain embodiments, the anterior side wall can have a convex shape and the posterior side wall can have a concave shape. In certain embodiments, each of the anterior side wall and the posterior side wall can have a substantially flat shape.

In certain embodiments, a tunnel can be formed through the intervertebral support structure. The tunnel can be formed in some embodiments between the anterior wall and the posterior wall of the intervertebral support structure. The tunnel can have a tensile strength that can resist inflation of the implant such that intervertebral support structure can be inhibited from having a spherical or cylindrical shape between the anterior wall and the posterior wall. In certain embodiments, the tunnel can be formed between the superior bearing surface and the interior bearing surface of the intervertebral support structure. The tunnel can have a tensile strength that can resist inflation of the implant such that the intervertebral support structure can be inhibited from having a spherical or cylindrical shape between the superior bearing surface and the interior bearing surface.

In some embodiments, the method can include coupling the inflatable implant to an implant holding device. Such a device can be utilized to insert the implant into, e.g., an intervertebral disc space. Further, in some embodiments the inflatable implant can be made of a porous material. In some embodiments, the inflatable implant can have a textured outer surface. In certain embodiments, the intervertebral support structure can be a fusion cage.

In another aspect, an inflatable implant is provided that can include an inflatable hollow body. The hollow body can be inflated to form an intervertebral support structure configured to fill an intervertebral space between anterior portion of adjacent vertebral bodies.

As with the aspects and embodiments described above, a number of additional or alternative features can be included that are considered within the scope of the present disclosure. For example, in some embodiments, the intervertebral support structure can include an anterior side wall having a first shape, a posterior side wall having a second shape, a superior bearing surface and an inferior bearing surface, a lateral end wall and a medial end wall. Each bearing surface can extend transversely between the anterior wall and the posterior wall. In certain embodiments, the anterior side wall can have a convex shape and the posterior side wall can have a concave shape. In certain embodiments, each of the anterior side wall and the posterior side wall can have a substantially flat shape.

In certain embodiments, a tunnel can be formed through the intervertebral support structure. The tunnel can be formed between the anterior wall and the posterior wall of the intervertebral support structure in certain embodiments. The tunnel can have a tensile strength that can resist inflation of the hollow body, such that the intervertebral support structure can be inhibited from having a spherical or cylindrical shape between the anterior wall and the posterior wall. In some embodiments, the tunnel can be formed between the superior bearing surface and the inferior bearing surface of the intervertebral support structure. The tunnel can have a tensile strength that can resist inflation of the hollow body, such that the intervertebral support structure can be inhibited from having a spherical or cylindrical shape between the superior bearing surface and the inferior bearing surface.

In some embodiments, the hollow body can be inflated with a curable material. Further, the hollow body of the inflatable implant can be configured to be rolled, folded, or collapsed when not inflated. In some embodiments, an implant holding device can be coupled to the implant. The hollow body can be made of a porous material in certain embodiments. In some embodiments, the hollow body can have a textured outer surface. In certain embodiments, the intervertebral support structure can be a fusion cage.

Any of the features or variations described above can be applied to any particular aspect or embodiment of the present disclosure in a number of different combinations. The absence of explicit recitation of any particular combination is due solely to the avoidance of repetition in this summary.

DETAILED DESCRIPTION

Figure 1A:
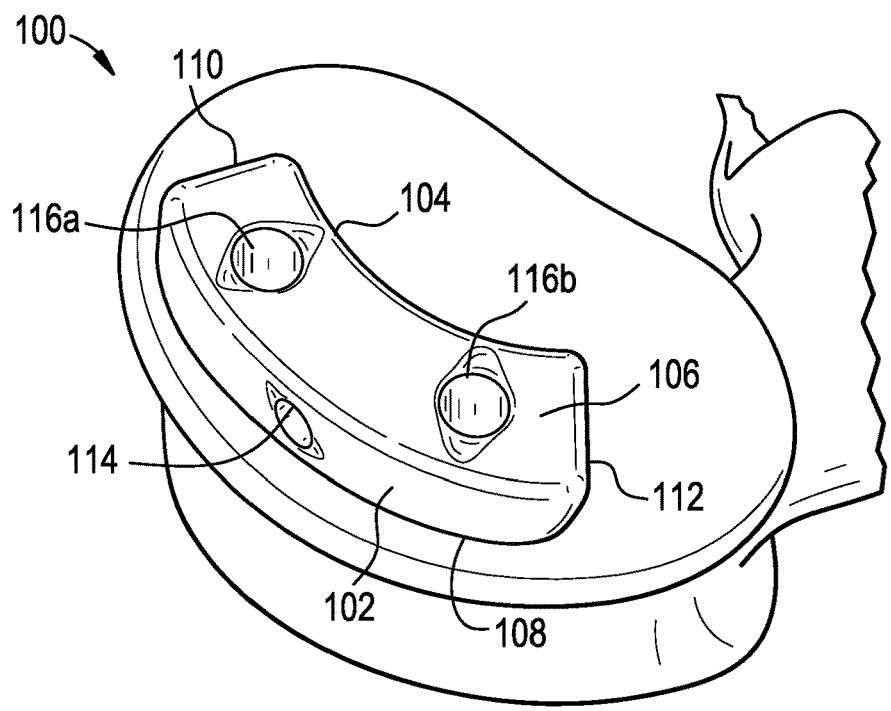
FIG. 1A is a schematic illustration of a perspective view of one embodiment of an inflatable orthopedic implant in an inflated state.
Figure 1B:
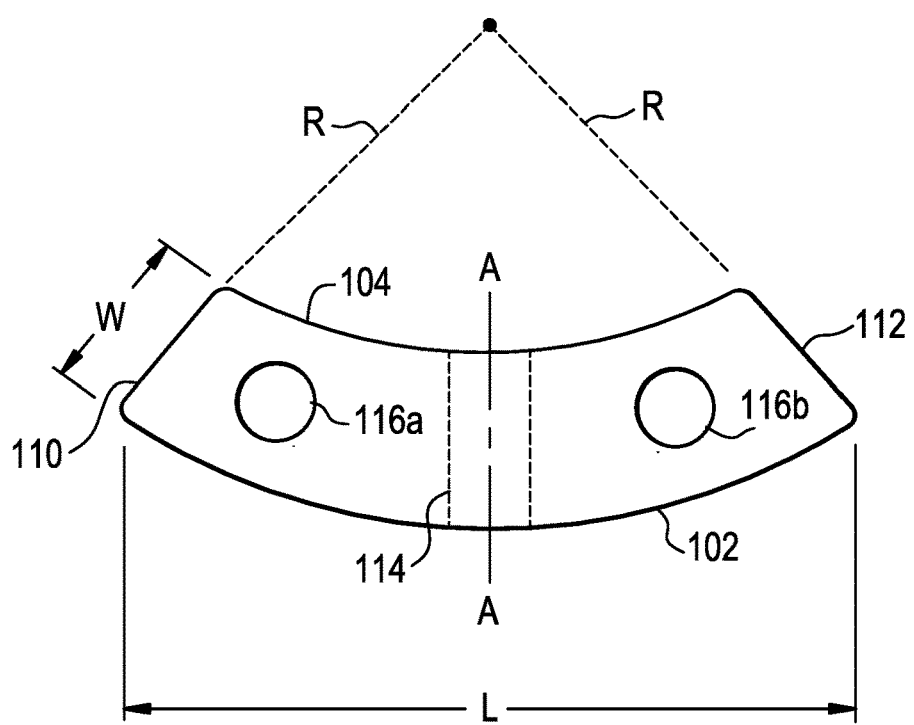
FIG. 1B is a schematic illustration of a top view of the inflatable implant of FIG. 1A in an inflated state.
Figure 1C:
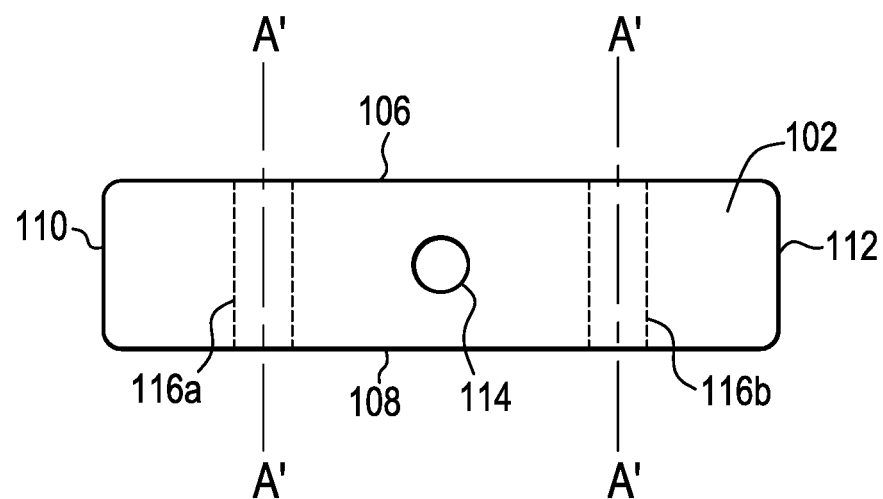
FIG. 1C is a schematic illustration of a side view of the inflatable implant of FIG. 1A in an inflated state.
Figure 1D:
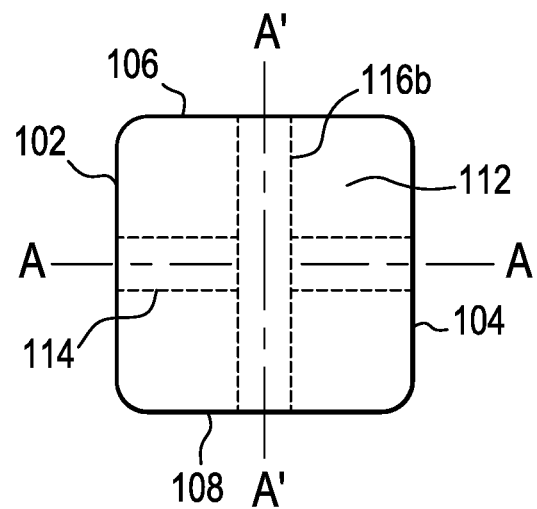
FIG. 1D is a schematic illustration of an end view of the inflatable implant of FIG. 1A in an inflated state.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Various embodiments of inflatable orthopedic implants and related methods for deploying such implants within an intervertebral space are described herein, e.g., for use in spinal fusion surgery, other intervertebral surgical procedures, or other surgical procedures. In various embodiments, the inflatable intervertebral implant can include a hollow inflatable body that can be configured in a compact state for insertion into a target intervertebral space between a pair of adjacent vertebral bodies. Once the vertebral bodies are separated or distracted, e.g., using one or more inflatable distractors, the hollow body of the inflatable implant can be inflated with bone cement or other curable material. When the curable material hardens, the inflated implant can form a rigid intervertebral support structure (e.g., a fusion cage) that is capable of maintain the vertebral distraction and thereby enabling removal of the distractors. In some embodiments, an inflatable implant can be deployed for corrective angulation between adjacent vertebral bodies. Such angular correction can be useful to reverse various deformities of the spine, including but not limited to scoliosis or other conditions that produce abnormal lordotic, kyphotic, or other spinal angles. In some embodiments, an inflatable orthopedic implant can be deployed in an intervertebral space in a minimally invasive manner. Although the inflatable orthopedic implants are disclosed for use in spinal fusion surgery, one skilled in the art will recognize that the inflatable implants can be readily modified and deployed for use in other intervertebral surgical procedures, or other surgical procedures in other portions of the body.

FIGS. 1A-1D are schematic illustrations of one exemplary embodiment of an inflatable orthopedic implant 100 in an inflated state. In the illustrated embodiment, the implant 100 has a hollow body configured to form an intervertebral support structure when inflated. The hollow body of the implant 100 can be inflated with a curable material or substance that hardens so that the inflated implant 100 can form a rigid intervertebral support structure. In some embodiments, the curable material used to inflate the implant can include, but is not limited to, a bone cement, PMMA (polymethyl methacrylate), PLA (polylactic acid) PDLA (poly-d-lactic acid), PLLA (poly-1-lactic acid), PEU (polyester urethane), PCL (polycaprolactone), calcium phosphates including calcium phosphate cements/composites involving fiber reinforcement, PLGA (polylactic-co-glycolic acid), bio-silks, and composites of the materials, for example. In some embodiments, the implant can be inflated with an elastic filler material or substance, such as but not limited to 2K-Silicon. The elastic filler material or substance can allow the inflated implant 100 to form an intervertebral support structure having a degree of flexibility to provide a dampening feature and therefore functionally substitute a healthy disc.

As shown, the implant 100 can be inflated to have a generally arcuate shape adapted to fill an intervertebral space between anterior portions of adjacent vertebral bodies. For example, the arcuate shape can be adapted to conform to the arcuate shape of the cortical rim that protrudes into the intervertebral space along the anterior portion of each endplate of the adjacent vertebral bodies. Thus, as discussed in more detail below, the arcuate shape of the inflated implant 100 can allow the implant to be deployed between adjacent vertebral bodies along or in close proximity to the anterior rims of the respective endplates. The bone strength of the endplate of a vertebral body is typically stronger at or surrounding the cortical rim. The intervertebral support structure formed by the inflated implant 100 can be used as a fusion cage for spinal fusion surgery.

In the illustrated embodiment, the intervertebral support structure formed by the inflated implant 100 includes an anterior side wall 102, a posterior side wall 104, a superior bearing surface 106, an inferior bearing surface 108, lateral end walls 110, 112. The anterior side wall 102 can have a convex shape and the posterior side wall 104 can have a concave shape. Each of the superior and inferior bearing surfaces 106, 108 can have an arcuate shape that extends transversely between the anterior and posterior side walls 102, 104. The lateral end walls 110, 112 can have a generally rectangular shape that defines the lateral ends of the implant.

Alternatively, in other embodiments, the implant 100 can be configured such that, when inflated, the anterior side wall 102 and the posterior side wall 104 can each have a different shape from the above-mentioned convex and concave shapes. For example, in some embodiments any of the anterior side wall 102 and the posterior side wall 104 can have a substantially flat or planar shape, e.g., for surgical procedures in which the implant is inserted into the intervertebral space using a lateral approach. In still other embodiments, additional surface shapes can be employed based on a variety of factors, such as desired final implant shape, implantation approach or method, etc.

The dimensions of the intervertebral support structure formed by the inflated implant 100 can depend on the dimensions of the bony anatomy of the vertebral endplates that bound the target intervertebral space. In some embodiments, the dimensions of the inflated implant 100 may be configured to allow the implant to be deployed between adjacent vertebral bodies along or in close proximity to the anterior rims of the respective vertebral endplates. For example, in some embodiments, the length L of the inflated implant 100 can range between approximately 20 millimeters (mm) and approximately 80 mm; the width W of the inflated implant 100 can range between approximately 8 mm and approximately 25 mm; the height H of the inflated implant 100 can range between approximately 6 mm and approximately 16 mm; and the radius of curvature R of the inflated implant 100 can range between approximately 10 mm and approximately 50 mm.

In some embodiments, the hollow body of the inflatable implant 100 can be configured to form tunnels or passageways that extend through the implant when inflated. One or more of the tunnels can be configured to have a tensile strength that resists inflation of the implant 100 in one or more directions to control the inflated shape of the implant. For example, in the illustrated embodiment, the implant 100 includes a tunnel 114 that extends through the anterior and posterior walls 102, 104. The tunnel 114 can be configured to have a tensile strength that resists inflation of the implant in an anterior-posterior direction A-A to inhibit, if not prevent, the walls from inflating into a spherical or cylindrical shape. Accordingly, the tunnel 114 facilitates inflation of the implant such that the arcuate shape of the implant between the anterior and posterior walls 102, 104 is maintained.

Alternatively or additionally, and as shown in the illustrated embodiment, the implant 100 can include one or more tunnels 116a, 116b (collectively 116) that extend through the superior and inferior bearing surfaces 106, 108. The tunnels 116 can be configured to have a tensile strength that resists inflation of the implant in a superior-inferior direction A'-A' to inhibit, if not prevent, the bearing surfaces 106, 108 from inflating into a spherical or cylindrical shape. Accordingly, the tunnels 116 facilitate inflation of the implant such that the substantially planar shape of bearing surfaces 106, 108 is maintained. The tunnels 114 and/or 116 can also be useful to facilitate bone growth through the implant.

In some embodiments, the tunnels 114 and/or 116 can be utilized to form internal tethers that can aid in controlling or biasing the shape of the implant 100, e.g., by limiting expansion of the implant in one or more directions. The tunnels 114 and/or 116 can be integrally formed with the other implant surfaces to provide an uninterrupted shell or envelope that defines the implant. Note that, in some embodiments, a shape of the implant 100 can alternatively or additionally be controlled or biased using one or more internal tethers extending between implant surfaces without forming a tunnel, e.g., a structure that defines a passage through the implant.

In some embodiments, the hollow body of the inflatable implant 100 can be made of a porous material. Minute spaces or holes in the porous material can allow air to escape during inflation, thereby reducing, if not preventing, the formation of air pockets that may weaken the rigid intervertebral support structure formed by the inflated implant. Alternatively or additionally, in some embodiments, the hollow body of the inflatable implant 100 can have a rough or otherwise textured surface. The textured surface of the inflatable implant 100 can be useful to increase friction between the bearing surfaces 106, 108 and the respective endplates of the adjacent vertebral bodies, thereby reducing migration of the inflated implant once deployed. In some embodiments, the porous material of the implant 100 can include, but need not be limited to, a braided fabric, a woven fabric (e.g., a three-dimensional woven fabric), a perforated foil or sheet, felt, or any combination thereof.

Figure 2A:
FIG. 2A is a schematic illustration of a side view of one embodiment of an inflatable orthopedic implant in a non-inflated state.
Figure 2B:
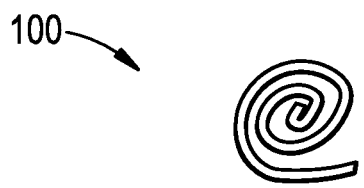
FIG. 2B is a schematic illustration of a side view of another embodiment of an inflatable orthopedic implant in a non-inflated state.
Figure 2C:
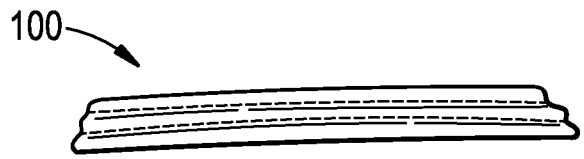
FIG. 2C is a schematic illustration of a side view of another embodiment of an inflatable intervertebral implant in a non-inflated state.

In some embodiments, the inflatable orthopedic implant 100 can be inserted into a target intervertebral space in a non-inflated, compact state. For example, as shown in the illustrated embodiment of FIG. 2A, the hollow body of the inflatable implant 100 can be folded. As shown in the illustrated embodiment of FIG. 2B, the hollow body of the inflatable implant 100 can be rolled. As shown in the illustrated embodiment of FIG. 2C, the hollow body of the inflatable implant 100 can be collapsed. In each of the foregoing embodiments, the surgeon or other medical staff can deliver the non-inflated implant 100 to the target space through a rigid or flexible cannula, access port, or other access device having a narrow diameter. By configuring the non-inflated implant in a compact state, the implant can be easily positioned to a desired location within the intervertebral space prior to inflation despite narrow space constraints.

Figure 2D:
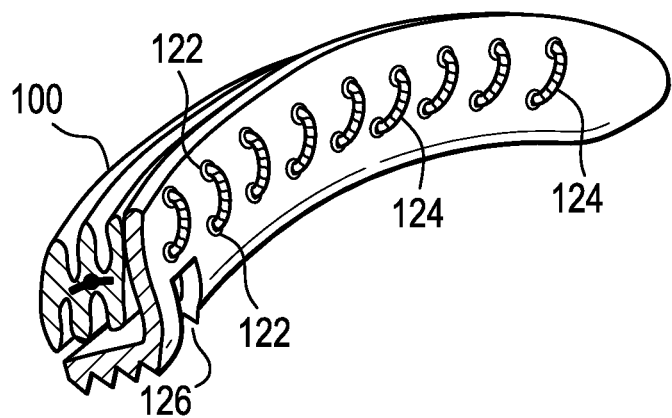
FIG. 2D is a schematic illustration of a perspective view of another embodiment of an inflatable intervertebral implant in a non-inflated state.

As shown in the illustrated embodiment of FIG. 2D, the inflatable orthopedic implant 100 can be coupled to an implant holding device 120. The implant holding device 120 can serve as a rigid support or backing for inserting the implant 100 into the intervertebral space. In some embodiments, the implant holding device 120 can be an L-shaped bracket. The implant holding device 120 can be coupled to the inflatable implant 100 using one or more sutures 122 looped through one or more suture holes 124 defined in the body of the holding device 120. In other embodiments, an inflatable implant can be coupled to the holding device 120 using other mechanisms, including without limitation, a biocompatible glue, or other adhesive. In the illustrated embodiment, the implant holding device 120 is configured to have a concave shape in order to prevent the device from inhibiting inflation of the implant 100 to have an arcuate shape. The implant holding device 120 can also include a notch 126 or other coupling mechanism for detachably coupling the holding device to an implant insertion instrument.

FIG. 3A-3J are schematic illustrations of one exemplary embodiment of a method of deploying an inflatable orthopedic implant. In the illustrated embodiment, the inflatable orthopedic implant 100 of FIG. 1A is deployed as part of an intervertebral surgical procedure for spinal fusion. Although the inflatable implant 100 of FIG. 1A is shown in the figures for purposes of example, in some embodiments the inflatable orthopedic implant can be modified to form different geometrical support structures when inflated.

Figure 3A:
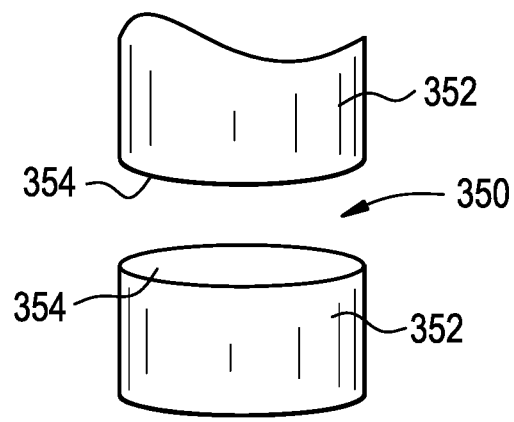
FIGS. 3A-3J are schematic illustrations of one exemplary method of deploying an inflatable orthopedic implant.

As shown in FIG. 3A, a target intervertebral space 350 is located between respective endplates 354 of an adjacent pair of superior and inferior vertebral bodies 352. Prior to deploying the implant 100, the target intervertebral space 350 can be cleared of any damaged intervertebral disc. When the natural disc is removed, the adjacent vertebral bodies 352 may collapse upon each other, thereby requiring separation of the vertebral bodies to deploy the inflatable orthopedic implant 100 within the intervertebral space 350. Alternatively, even if there is no collapse associated with removal of the existing disc material, the intervertebral space can be compressed as compared to desired spacing due to the above-described degeneration. Accordingly, for a number of reasons it can be desirable to distract the two vertebral bodies 352 to achieve a desired intervertebral spacing.

Figure 3B:
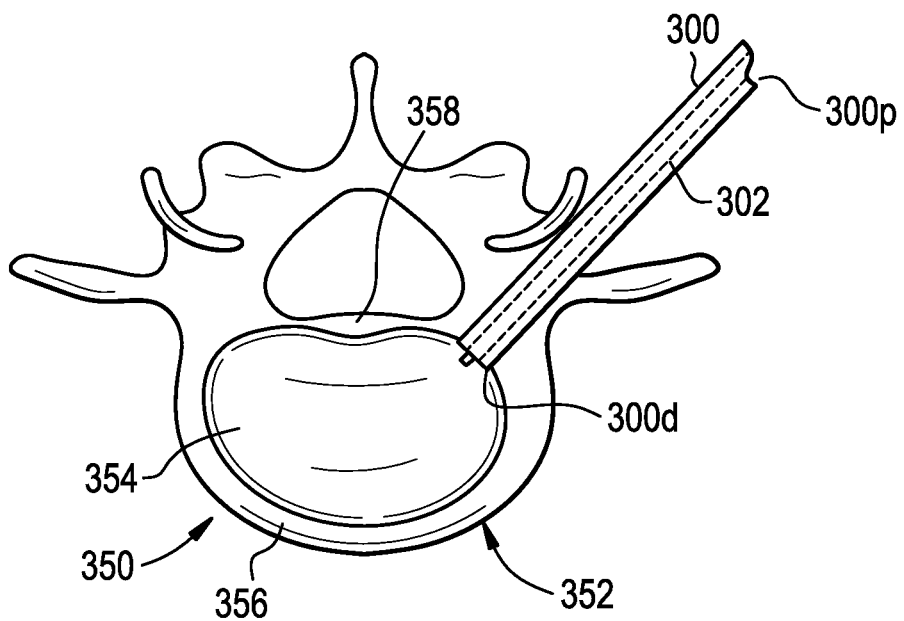

As shown in FIG. 3B, an access device 300 can be percutaneously inserted into the intervertebral space 350. The access device 300 can have a proximal end 300p and a distal end 300d and at least one lumen 302 that extends between the proximal and distal ends. In some embodiments, the access device 300 can include, without limitation, a flexible or rigid cannula, access port, or other tubular working channel, for example. In the illustrated embodiment, the access device 302 can be percutaneously inserted into the intervertebral space 350 using a transforaminal approach. However, in various embodiments the access device 300 can be delivered to the intervertebral space 350 using other surgical approaches, including, without limitation, a lateral approach, a posterior approach, an anterior approach, and a posterolateral approach. The access device 300 can have a narrow width or diameter to minimize invasiveness of the intervertebral surgical procedure. In some embodiments, the outer width or diameter of the access device 300 can range between approximately 3 millimeters (mm) and 9 mm (e.g., 6 mm).

Figure 3C:
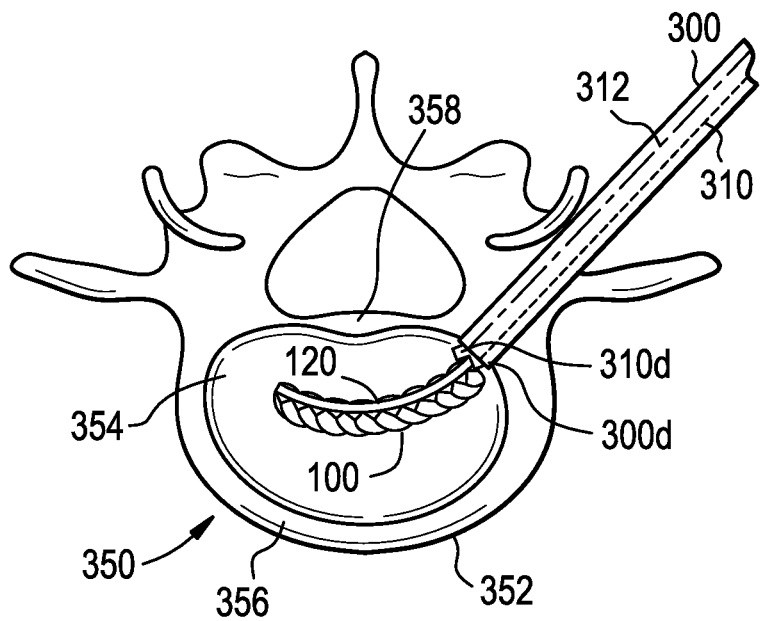

As shown in FIG. 3C, the inflatable implant 100 can be inserted into the intervertebral space 350 in a non-inflated state. In some embodiments, the inflatable implant 100 can be inserted within the intervertebral space 350 between the anterior portions of the adjacent vertebral bodies 352 where bone strength is typically strong and thus the risk of fracture is reduced. For example, the inflatable implant 100 can be inserted between the adjacent vertebral bodies 352 along or in close proximity to the anterior rims 356 of the respective vertebral endplates 354.

In the illustrated embodiment, the inflatable implant 100 is inserted into the intervertebral space 350 through the distal end 300d of the access device 300. As discussed above with respect to FIGS. 2A-2D, the inflatable implant 100 can be rolled, folded, collapsed, or otherwise compacted to navigate the implant through the narrow space constraints of the access device 300 and the intervertebral space 350. The inflatable implant 100 can be coupled to the distal end of a fill tube 312 that extends through the access device 300. The fill tube 312 is used as a fluid conduit for flowing a curable material to inflate the hollow body of the implant 100.

In the illustrated embodiment, an elongated insertion instrument 310 can be used to insert the inflatable implant 100 into the intervertebral space 350. For example, as shown in FIG. 3C, the elongated insertion instrument 310 can have a distal end 310d that is detachably coupled to an implant holding device 120. The implant holding device 120 can be attached to the inflatable implant 100 for support as discussed above with respect to FIG. 2D. The distal end 310d of the instrument can be detachably coupled to the implant holding device 120 using a clasp, latch, hook, clip or other detachable coupling mechanism. The insertion instrument 310 can be used to push the implant holding device 120 along with the attached implant 100 through the access device 300 and into the intervertebral space 350. However, in some embodiments other insertion instruments can be used to insert the inflatable implant 100 into the target intervertebral space 350. For example, in some embodiments, a removable guide wire or stylet can be used to push the implant through the access device 300 and to a desired location within the intervertebral space 350.

Figure 3D:
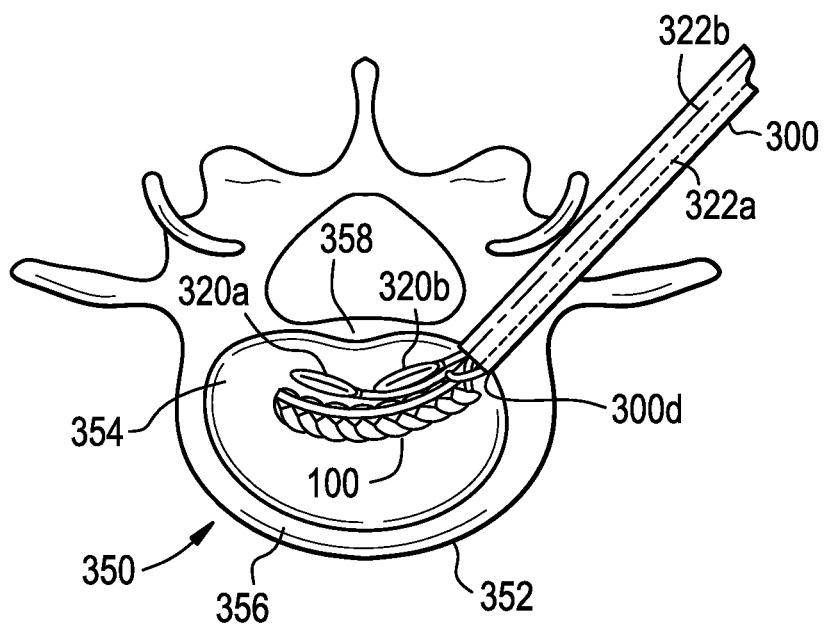

As shown in FIG. 3D, inflatable distractors 320a and 320b (collectively 320) can be inserted into the intervertebral space 350 in a non-inflated state. For example, in some embodiments, the distractors 320 can be balloons. The inflatable distractors 320 can be inserted within the intervertebral space 350 between the posterior portions of the adjacent vertebral bodies 352 where bone strength is typically strong and thus the risk of fracture is less. For example, in some embodiments, the inflatable distractors 320 can be inserted between the adjacent vertebral bodies 352 along or in close proximity to the posterior rim 358 of the respective vertebral endplates 354. The inflatable distractors 320 can be inflated to exert a distraction force against the posterior portions of the adjacent vertebral bodies 352 and thereby create a separation or distraction between the adjacent vertebral bodies.

In the illustrated embodiment, the inflatable distractors 320 are inserted into the intervertebral space 350 through the distal end 300d of the access device 300. For example, the inflatable distractors 320 can be inserted into the intervertebral space 350 serially. In some embodiments, the inflatable distractors 320 can be inserted into the intervertebral space 350 before insertion of the inflatable implant 100. Each of the inflatable distractors 320a, 320b can be coupled to the distal end of a respective fill tube 322a and 322b (collectively, fill tubes 322). The fill tubes 322 can be used as fluid conduits for flowing a gas or liquid to individually inflate the distractors 320. In some embodiments, the inflatable distractors 320 can be inserted into the intervertebral space 350 using removable guide wires (not shown) inserted through the respective fill tubes 322.

Although two inflatable distractors 320a and 320b are shown for purposes of example in the figures, in some embodiments fewer or greater than two inflatable distractors can be inserted into the intervertebral space 350 for distracting the adjacent vertebral bodies (e.g., one distractor, three distractors, etc.).

In some embodiments, a guide (not shown) can be inserted into the intervertebral space 350 to partition the respective anterior and posterior portions of the intervertebral space and thereby facilitate alignment of the inflatable implant 300 and the inflatable distractors 320 into the respective anterior and posterior portions of the target space. The guide can also be useful to avoid migration of the inflatable implant 300 and the inflatable distractors 320 during inflation. In some embodiments, the guide can be a rail disposed at the distal end of a stylet or other elongated instrument.

Figure 3E:
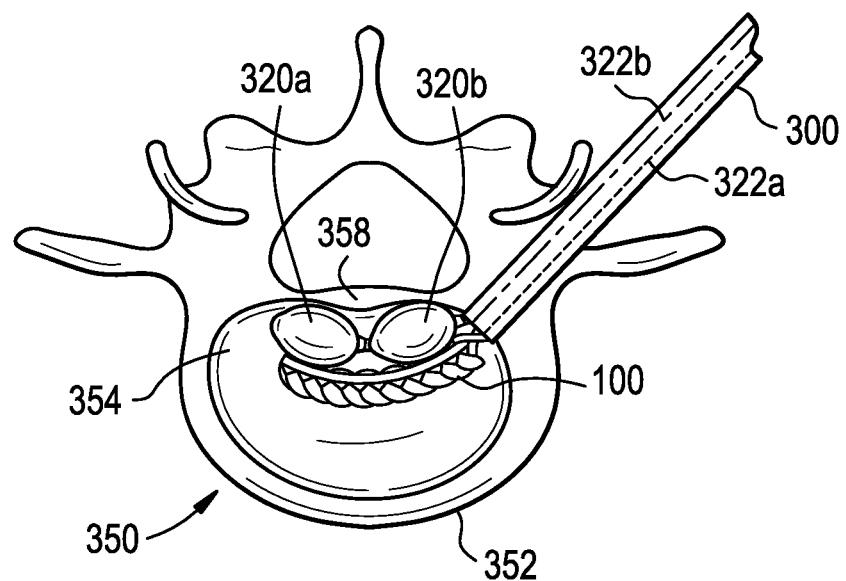

As shown in FIG. 3E, the inflatable distractors 320 can be inflated to exert a force against the posterior portions of the adjacent vertebral bodies 352 such that the vertebral bodies can become distracted or separated. For example, in the illustrated embodiment, the distractors 320 are inflated at or in close proximity to the posterior rims 358 of the respective endplates 354. By inflating the distractors 320 in the posterior region of the intervertebral space 350, greater changes in angular distraction can be made between the adjacent vertebral bodies 352 in response to relatively smaller changes in distractor size as compared to embodiments where the distractors are placed elsewhere with regard to the vertebrae. Alternatively or additionally, by inflating the distractors 320 in the posterior region of the intervertebral space 350, the rotational moment of the vertebral bodies 352 can be reduced during inflation and thereby facilitate improved control over the distraction of the vertebral bodies.

The inflatable distractors 320 are configured to be inflated to internal pressures that are equal to or greater than the external load applied between the adjacent vertebral bodies 352. For example, in some embodiments, the distractors 320 can be inflated to a maximum internal pressure in the range between approximately 2 bars and approximately 30 bars. By inflating the distractors 320 to internal pressures that exceed the external load applied by the adjacent vertebral bodies 352, the distractors can expand to sizes (e.g., diameters) that exert forces which create separation or distraction between the vertebral bodies.

In some embodiments, the distractors 320 can be inflated to respective sizes which separate or distract the adjacent vertebral bodies 352 by a desired height. In some embodiments, the distractors 320 can be inflated to the same or different sizes to adjust an angle between adjacent vertebral bodies 352 in one or more of a frontal plane (i.e., a plane that divides the body into anterior and posterior parts) and a sagittal plane (i.e., a plane that divides the body into right and left parts). For example, in some embodiments, the distractors 320 can be inflated to have at least a minimum size (e.g., diameter) for adjusting an angle between the adjacent vertebral bodies 352 in the sagittal plane (e.g., a lordotic angle). Alternatively or additionally, the distractors 320 can be inflated to different sizes to adjust an angle between the adjacent vertebral bodies 352 in the frontal plane (e.g., a Cobb angle). Thus, the distractors 320 can be inflated to respective sizes that create angular distractions or separations between adjacent vertebral bodies in order to correct various deformities in the curvature of the spine, e.g., scoliosis or other abnormal lordotic, kyphotic, or other spinal angles.

In some embodiments, the distractors 320 can be inflated by flowing a non-curable liquid, gas, or other substance through the fill tubes 322 into the distractors 320. For example, the distractors 320 can be balloons inflated by flowing a saline solution through the fill tubes 322 into the distractors 320. In some embodiments, the balloons can be made of a polymer material that can be inflated to a maximum internal pressure greater than the external load applied between the adjacent vertebral bodies 352 (e.g., approximately 20 bars or more).

Figure 3F:
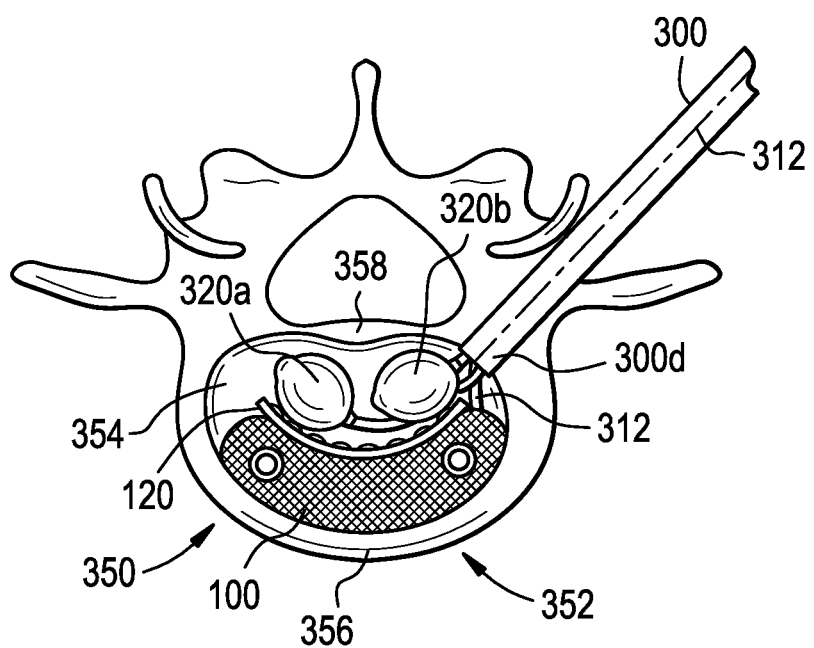

As shown in FIG. 3F, while the inflated distractors 320 maintain the desired distraction or separation between the adjacent vertebral bodies 352, the inflatable implant 100 can be inflated. The implant 100 can be inflated by flowing bone cement or other curable material through the fill tube 312 into the hollow body of the implant. As shown in the illustrated embodiment, the inflatable implant 100 can be configured to generally form the intervertebral support structure shown and described with respect to FIGS. 1A-1D. For example, as shown, the intervertebral support structure formed by the inflated implant 100 can have an arcuate shape that fills the intervertebral space between the anterior portions of the adjacent vertebral bodies. In some embodiments, the implant 100 can be inflated until the superior and inferior bearing surfaces (e.g., 106, 108) of the implant bear against and preferably conform to the respective vertebral endplates 354 of the adjacent vertebral bodies 352 (e.g., at or in close proximity to the anterior rim 356). After the implant 100 is inflated the fill tube 312 can be cut or otherwise disconnected from the implant.

As the implant 100 is inflated, the inflated distractors 320 can continue to exert a force on the adjacent vertebral bodies 352 to maintain the desired distraction or separation. Thus, the inflated distractors 320 can shield the implant 100 from the applied load of adjacent vertebral bodies 352 while the implant inflates and cures. Once the bone cement or other curable material hardens, the inflated implant 100 can form a rigid intervertebral support structure capable of withstanding the applied load of the adjacent vertebral bodies 352. Thus, once hardened, the inflated implant 100 can support the distraction or separation of the vertebral bodies without the inflated distractors 320.

Because the distraction of the vertebral bodies 352 can be supported by the rigid support structure of the inflated implant 100, the implant 100 can be inflated with the curable material to a lower internal pressure than the internal pressure(s) of the inflated distractors 320 used to initially set the distraction. In some embodiments, the implant 100 can be inflated to an internal pressure that does not exert a force capable of distracting or separating the vertebral bodies 352. For example, the inflatable implant 100 can be configured to inflate to a maximum internal pressure that is less than the external load applied between the adjacent vertebral bodies 352. Rather, the implant 100 can be inflated to a lower internal pressure that allows the hollow body of the implant to fill the intervertebral space between the vertebral endplates 352 of the adjacent bodies. For example, in some embodiments, the inflatable implant 100 can be inflated to a maximum internal pressure less than approximately 20 bar, e.g., approximately 1 or 2 bar. With a lower requirement for maximum internal pressure, the inflatable implant 100 can be made of a biocompatible polymer or other suitable material that may rupture at higher pressures needed to distract or separate adjacent vertebral bodies.

Figure 3G:
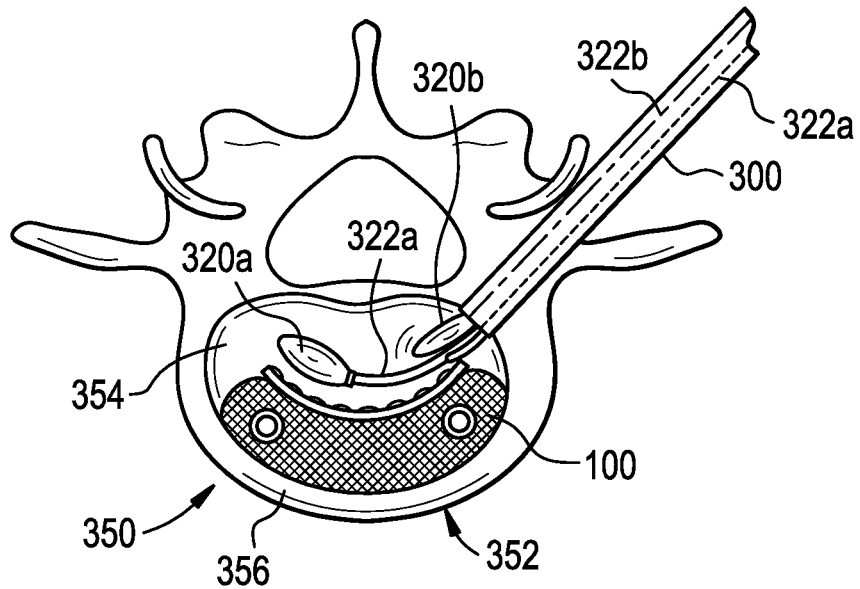

As shown in FIG. 3G, after the inflated implant 100 hardens into a rigid intervertebral support structure, the inflated distractors 320 can be deflated and withdrawn from the intervertebral space 350. For example, in some embodiments, the inflated distractors 320 can be deflated by suctioning the saline solution or other non-curable material out of the distractors 320. Once deflated, the distractors 320 can be removed from the intervertebral space 350 by withdrawing the fill tubes 322 proximally from the access device 300. The inflated implant 100 can remain within the intervertebral space 350 to provide support between the anterior portion of the adjacent vertebral bodies 352 after withdrawal of the distractors 320.

Figure 3H:
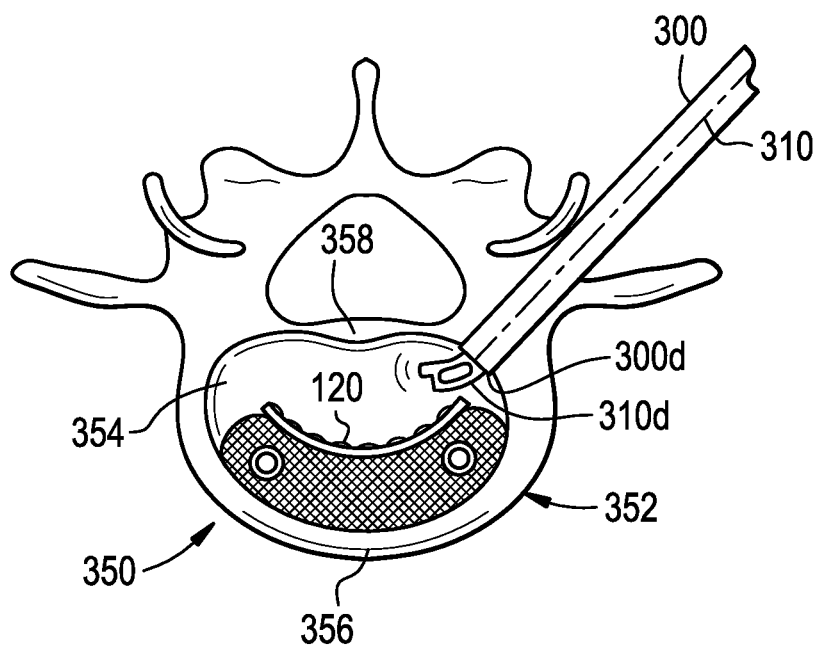

As shown in FIG. 3H, the elongated insertion instrument 310 used to insert the inflatable implant 100 can be removed. For example, and as shown in the illustrated embodiment, the distal end 310d of the elongated insertion instrument 310 can be detached from the implant holding device 120 used to support the inflatable implant 100. The distal end 310d of the instrument can be detached by releasing a clasp, latch, hook, clip, or other detachable coupling mechanism used to detachably couple the insertion instrument 310 to the implant holding device 120. Although the insertion instrument 310 is disclosed herein as being removed after the implant 100 is inflated and hardened, the insertion instrument 310 can be removed at any time. For example, where a removable guide wire or stylet is used to insert the implant 100 within the intervertebral space 350, the guide wire or stylet can be removed after the implant 100 is guided to a desired location within the space.

Figure 3I:
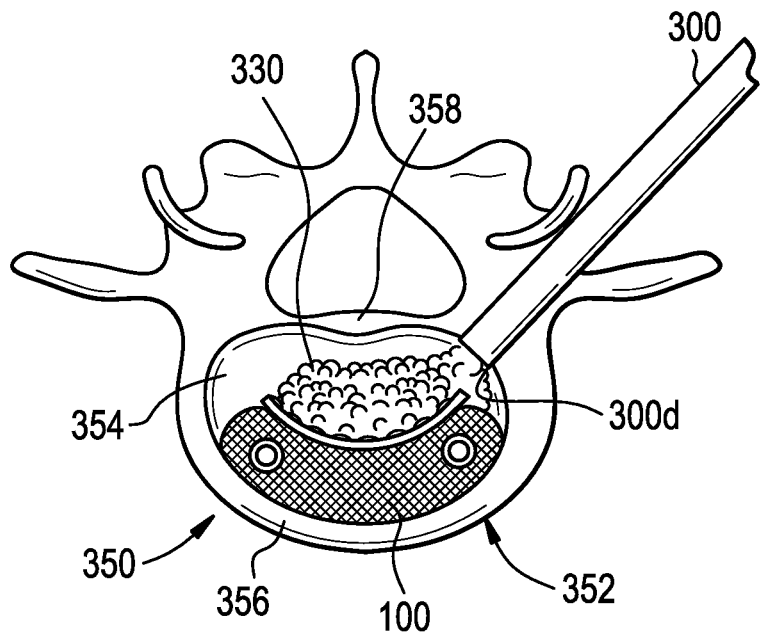
Figure 3J:
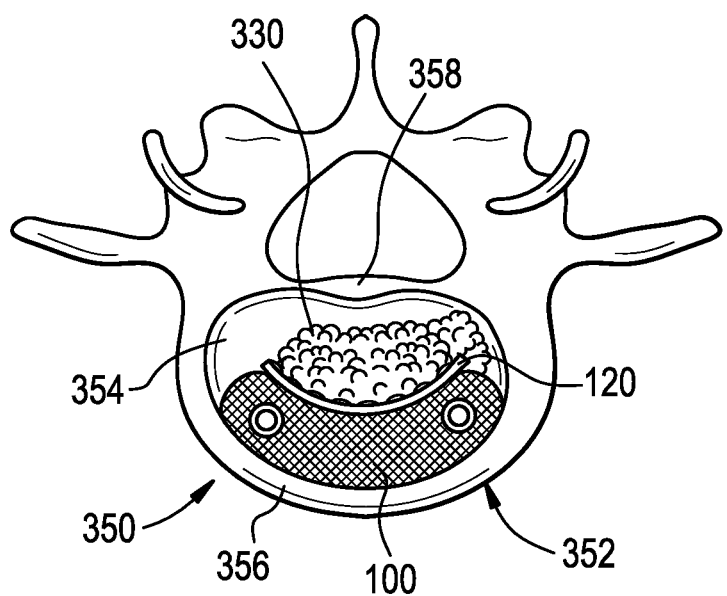

As shown in FIG. 3I, the intervertebral space 350 can be filled with a material 330 that facilitates fusion between the adjacent vertebral bodies 352. For example, in some embodiments, after the inflated implant 100 hardens into a rigid intervertebral support structure and the inflatable distractors 320 are withdrawn from the intervertebral space 350, bone graft, cancellous bone, or other fusion material 330 can be delivered into the space through one or more of the lumens 302 of the access device 300. After the fusion material 330 is delivered, the access device 300 can be withdrawn from the intervertebral space 350 as shown in FIG. 3J. Over time, the fusion material 330 can cause bone to form within the intervertebral space 350, and thereby cause the adjacent vertebral bodies 352 to fuse together between the endplates 354.

As previously discussed with respect to FIGS. 3A-3J, the inflatable implant 100 and the inflatable distractors 320 can be delivered to the intervertebral space 350 through an access device 300. In an effort to minimize the invasiveness of the intervertebral surgical procedure, the access device 300 can have a narrow width or diameter. For example, in some embodiments, the outer width or diameter of the access device 300 can range between approximately 3 millimeters (mm) and 9 mm (e.g., 6 mm). Delivery of the various components for deploying the inflatable implant 100 through such narrow dimensions can be challenging.

To facilitate such deployment, the inflatable implant 100 and the inflatable distractors 320 can be serially delivered through the lumen 302 of the access device 300. For example, as shown in the illustrated embodiment of FIGS. 4A-4E, the inflatable implant 100, the first inflatable distractor 320a, and the second inflatable distractor 320b can be inserted serially through the lumen 302 of the access device 300. Although FIGS. 4A-4E show the inflatable implant 100, the first inflatable distractor 320a, and the second inflatable distractor 320b being delivered in a specific order, these inflatable devices can be delivered serially in a different order.

Figure 4A:
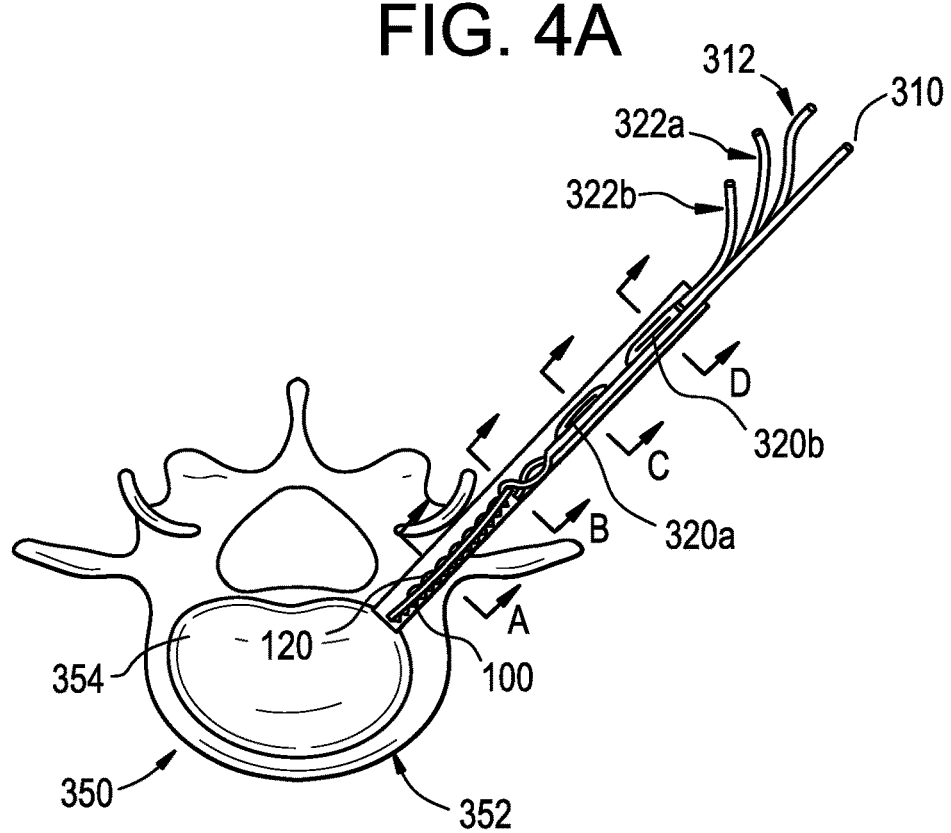
FIG. 4A is a schematic illustration of a longitudinal cross-sectional view of one exemplary embodiment of an access device, e.g., suitable for use in the method of FIGS. 3A-3J.
Figure 4B:
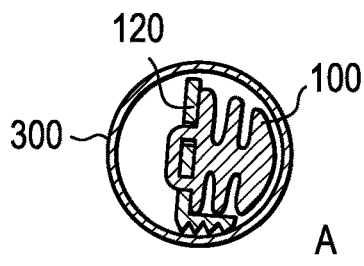
FIGS. 4B-4E are schematic illustrations of transverse cross-sectional views along the access device of FIG. 4A.
Figure 4C:
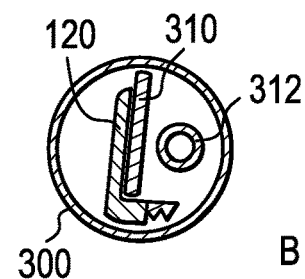
Figure 4D:
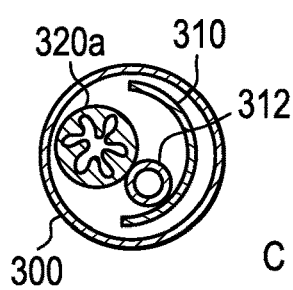
Figure 4E:
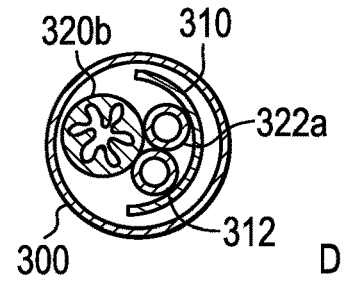

In some embodiments, the various devices being deployed through the access device 300 can be configured or shaped to provide more efficient use of space within the lumen 302. For example, as shown in FIGS. 4B and 4C, the implant holding device 120 can be used to compress the inflatable implant 100 to occupy less than the entire cross-sectional space in the lumen 302. Alternatively or additionally, as shown in FIGS. 4D and 4E, at least a portion of the elongated insertion instrument 310 used to insert the implant holding device 120 and the attached inflatable implant 100 can be a semi-circular tube having a C-shaped body. The arcuate body of the insertion instrument 310 can thus allow multiple components to occupy the same space. For example, as shown in FIG. 4D, the arcuate shaped insertion instrument 310 can occupy the same space as the first distractor 320a and the implant fill tube 312. As shown in FIG. 4E, the arcuate shaped insertion instrument 310 can occupy the same space as the second distractor 320b and the implant fill tube 312 and the fill tube 322a for the first distractor 320a.

Figure 5A:
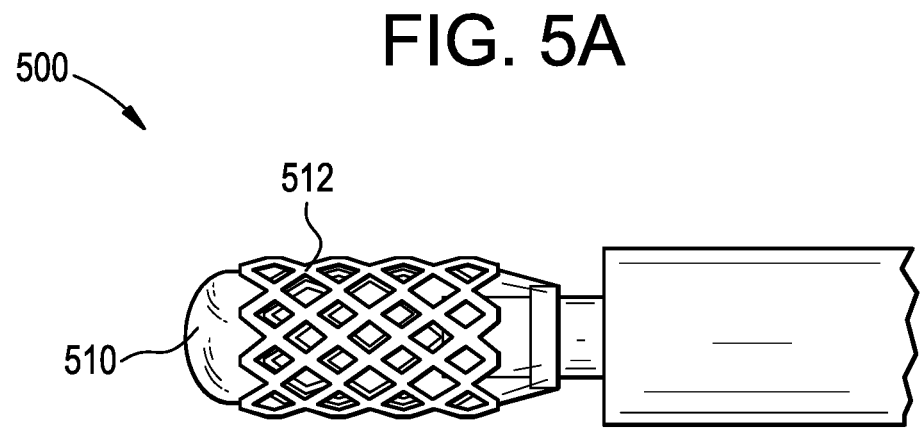
FIG. 5A is a schematic illustration of another embodiment of an inflatable orthopedic implant in an inflated state.

Although the inflatable intervertebral implant 100 of FIG. 1A is shown in the figures for purposes of example, in some embodiments the inflatable orthopedic implant can be modified to form different geometrical support structures when inflated. For example, as shown in FIG. 5A, the inflatable orthopedic implant 500 can include an inflatable balloon 510 that forms a substantially cylindrical support structure when inflated. The implant 500 can also include an expandable stent-like structure 512 that wraps around balloon 510. Like the inflatable implant 100, the balloon 510 can be filled with bone cement or other curable material that hardens to form a rigid support structure. The stent-like structure 512 can be useful to grip the bony end plates (e.g., 354) of adjacent vertebral bodies (e.g., 354) bounding the target intervertebral space. In some embodiments, the balloon 510 can have a mesh-like exterior to grip the bony end plates, and thereby avoiding the need for the stent-like structure.

Figure 5B:
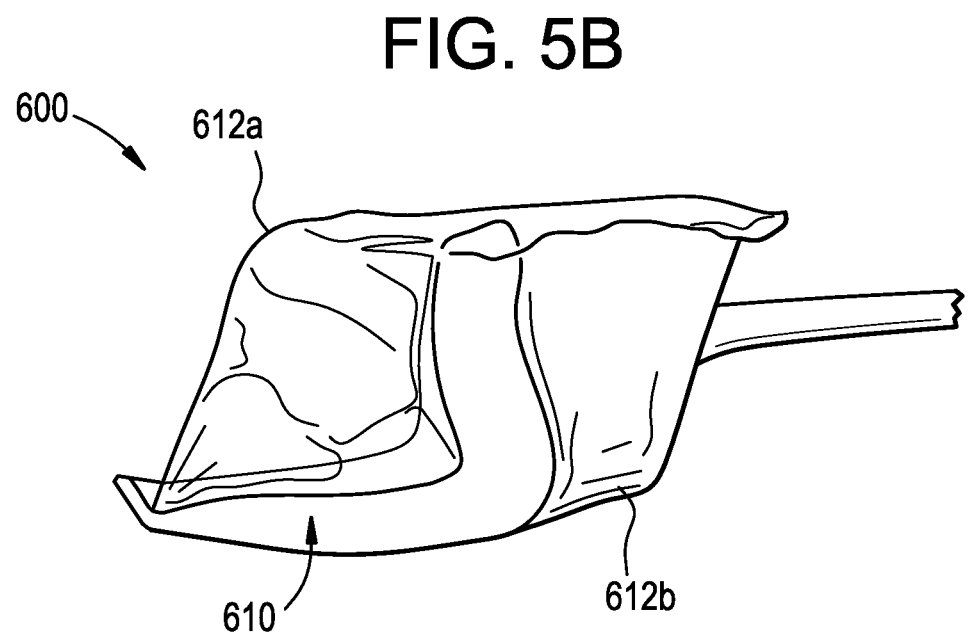
FIG. 5B is a schematic illustration of another embodiment of an inflatable intervertebral implant in an inflated state.

As shown in FIG. 5B, the inflatable orthopedic implant 600 can include a foil based balloon 610. For example, and as shown in the illustrated embodiment, the foil based balloon 610 can be fabricated using two or more polymer foil sheets 612a, 612b assembled together such that the balloon has a substantially rectangular shape when inflated with bone cement or other curable material. The non-distracting balloon can fill to its designed shape rather than to an unknown morphic shape. The balloon can be chosen as a corrective height and width by the surgeon to ensure a specific finished vertebral alignment. In some embodiments, the foil sheets can be made of a polyetheretherketone (PEEK) material. In some embodiments the balloon can be assembled together with arcuate panels to give an arcuate shape similar to implant 100.

Figure 5C:
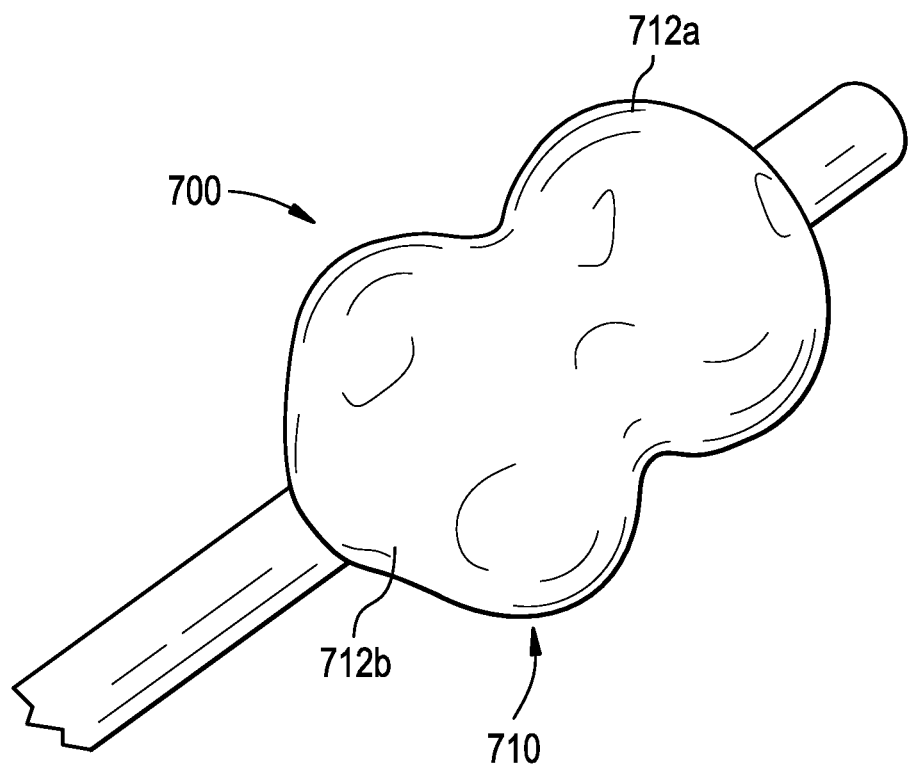
FIG. 5C is a schematic illustration of another embodiment of an inflatable intervertebral implant in an inflated state.

As shown in FIG. 5C, the inflatable orthopedic implant 700 can include a molded balloon 710 in some embodiments. For example, and as shown in the illustrated embodiment, the molded balloon can be configured to include two or more spherically shaped compartments 712a, 712b that can be filled with bone cement or other curable material.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described. Accordingly, the disclosure is not to be limited by what has been particularly shown and described. All publications and references cited herein are expressly incorporated herein by reference in their entirety.

The invention claimed is:

1. A method of deploying an inflatable implant, comprising:
   inserting, using an access device, an inflatable implant into an intervertebral space between anterior portions of adjacent vertebral bodies;
   inserting, using the access device, an inflatable distractor into the intervertebral space between posterior portions of the adjacent vertebral bodies;
   inflating the distractor such that the inflated distractor exerts a force against the posterior portions of the adjacent vertebral bodies and thereby separates the adjacent vertebral bodies; and
   inflating the implant after the distractor separates the adjacent vertebral bodies to form an intervertebral support structure having an arcuate shape that fills the intervertebral space between the anterior portions of the adjacent vertebral bodies,
   wherein the inflatable implant and the inflatable distractor are disposed serially in a lumen of the access device together before insertion.

2. The method of claim 1, wherein the implant is inflated with a curable material.

3. The method of claim 2, further comprising:
   deflating the inflated distractor within the intervertebral space after the inflated implant hardens; and
   withdrawing the deflated distractor from the intervertebral space,
   wherein the inflated implant remains within the intervertebral space to provide support between the anterior portions of the adjacent vertebral bodies after withdrawal of the distractor.

4. The method of claim 1, wherein the distractor is inflated to a size that separates the adjacent vertebral bodies by a desired height.

5. The method of claim 1, wherein inflating the distractor comprises inflating a plurality of distractors.

6. The method of claim 5 wherein each of the plurality of distractors is inflated to a respective size to adjust an angle between the adjacent vertebral bodies in a sagittal plane.

7. The method of claim 5, wherein each of the plurality of distractors is inflated to a respective size to adjust an angle between the adjacent vertebral bodies in a frontal plane.

8. The method of claim 1, further comprising:
filling the intervertebral space with a fusion material that facilitates bone growth between the adjacent vertebral bodies.

9. The method of claim 1, wherein the inflatable implant is rolled, folded, or collapsed when inserted into the intervertebral space.

10. The method of claim 1, wherein the inflatable implant, when inflated, forms the intervertebral support structure that comprises:
an anterior side wall having a first shape;
a posterior side wall having a second shape;
a superior bearing surface and an inferior bearing surface, each bearing surface extending transversely between the anterior wall and the posterior wall; and
a lateral end wall and a medial end wall.

11. The method of claim 10, wherein a body of the inflatable implant includes a tunnel integrally formed therethrough, and wherein the tunnel is configured to have a tensile strength such that the tunnel resists inflation of the inflatable implant in one or more directions to control a shape of the intervertebral support structure.

12. The method of claim 11, wherein the tunnel is formed between the anterior wall and the posterior wall of the intervertebral support structure.

13. The method of claim 11, wherein the tunnel is formed between the superior bearing surface and the interior bearing surface of the intervertebral support structure.

14. The method of claim 1, further comprising coupling the inflatable implant to an implant holding device.

15. The method of claim 1, wherein the inflatable implant is made of a porous material.

16. The method of claim 1, wherein the inflatable implant has a textured outer surface.

17. The method of claim 1, wherein the inflatable implant, when inflated, forms a fusion cage.

18. An inflatable implant, comprising:
an inflatable hollow body defining a first exterior surface and a second exterior surface opposite the first surface,
wherein the hollow body is inflated to form an intervertebral support structure configured to fill an intervertebral space between anterior portion of adjacent vertebral bodies,
wherein the inflatable hollow body includes a tunnel integrally formed therethrough, the first exterior surface defining a first opening to the tunnel and the second exterior surface defining a second opening to the tunnel, the tunnel extending from the first opening to the second opening, and
wherein the tunnel of the inflatable body defines a tensile strength such that the tunnel resists inflation of the inflatable hollow body in one or more directions to control a shape of the intervertebral support structure.

19. The inflatable implant of claim 18, wherein the intervertebral support structure comprises:
an anterior side wall having a first shape;
a posterior side wall having a second shape;
a superior bearing surface and an inferior bearing surface, each bearing surface extending transversely between the anterior wall and the posterior wall; and
a lateral end wall and a medial end wall,
wherein the first exterior surface comprises at least one of the anterior side wall, the lateral end wall, or the superior bearing surface, and wherein the second exterior surface comprises at least one of the posterior side wall, the medial end wall, or the inferior bearing surface.

20. The inflatable implant of claim 19, wherein the anterior side wall has a convex shape and the posterior side wall has a concave shape.

21. The inflatable implant of claim 19, wherein each of the anterior side wall and the posterior side wall has a substantially flat shape.

22. The inflatable implant of claim 19, wherein the tunnel between extends from the anterior wall to the posterior wall of the intervertebral support structure.

23. The inflatable implant of claim 19, wherein the tunnel extends from the superior bearing surface to the inferior bearing surface of the intervertebral support structure.

24. The inflatable implant of claim 18, wherein the hollow body is inflated with a curable material that hardens.

25. The inflatable implant of claim 18, wherein the hollow body of the inflatable implant is configured to be rolled, folded, or collapsed when not inflated.

26. The inflatable implant of claim 18, further comprising an implant holding device coupled to the implant.

27. The inflatable implant of claim 18, wherein the hollow body is made of a porous material.

28. The inflatable implant of claim 18, wherein the hollow body has a textured outer surface.

29. The inflatable implant of claim 18, wherein the intervertebral support structure is a fusion cage.

* * * * *